(12) United States Patent
Freiberg et al.

(10) Patent No.: US 10,195,006 B2
(45) Date of Patent: Feb. 5, 2019

(54) INTRAORAL DENTAL IRRIGATION APPLIANCE

(71) Applicants: Adam Wayne Freiberg, Littleton, CO (US); Joshua Wayne Freiberg, Littleton, CO (US)

(72) Inventors: Adam Wayne Freiberg, Littleton, CO (US); Joshua Wayne Freiberg, Littleton, CO (US)

(*) Notice: Subject to any disclaimer, the term of this patent is extended or adjusted under 35 U.S.C. 154(b) by 0 days.

(21) Appl. No.: 15/046,774

(22) Filed: Feb. 18, 2016

(65) Prior Publication Data
US 2016/0235509 A1    Aug. 18, 2016

Related U.S. Application Data

(60) Provisional application No. 62/117,638, filed on Feb. 18, 2015.

(51) Int. Cl.
*A61C 17/02*    (2006.01)
*A61C 17/00*    (2006.01)
*A61C 17/028*    (2006.01)

(52) U.S. Cl.
CPC ..........  *A61C 17/0211* (2013.01); *A61C 17/00* (2013.01); *A61C 17/02* (2013.01); *A61C 17/028* (2013.01)

(58) Field of Classification Search
CPC .......................... A61C 17/0211; A61C 17/228
See application file for complete search history.

(56) References Cited

U.S. PATENT DOCUMENTS

| | | | | |
|---|---|---|---|---|
| 3,379,192 A | * | 4/1968 | Warren, Jr. ........ | A61C 17/0211 601/164 |
| 5,443,386 A | * | 8/1995 | Viskup ............... | A61C 17/0211 433/216 |
| 5,890,895 A | * | 4/1999 | Tucker ................ | A61C 9/0006 433/37 |
| 2013/0260332 A1 | * | 10/2013 | Shapiro ............. | A61C 17/0211 433/80 |

* cited by examiner

*Primary Examiner* — Cris L Rodriguez
*Assistant Examiner* — Stephen Sparks
(74) *Attorney, Agent, or Firm* — Sheridan Ross P.C.

(57) ABSTRACT

An intraoral dental irrigation appliance is provided. The device can serve as a dual-purpose occlusal guard and irrigation device. The appliance can protect the teeth of the user from the damage caused by bruxism and even provide the user the ability to effectively irrigate some or all difficult areas of dentition. The appliance includes at least one port configured to receive an irrigation fluid, or irrigant. This port may attach to a fluid source like a tap, water irrigation device, or other moving fluid supply.

17 Claims, 8 Drawing Sheets

INTRAORAL DENTAL IRRIGATION APPLIANCE

CROSS REFERENCE TO RELATED APPLICATION

The present application claims the benefit of and priority, under 35 U.S.C. § 119(e), to U.S. Provisional Application Ser. No. 62/117,638, filed Feb. 18, 2015, entitled "Intraoral Dental Irrigation Appliance," the entire disclosure of which is hereby incorporated by reference, in its entirety, for all that it teaches and for all purposes.

FIELD OF THE DISCLOSURE

The present disclosure relates generally to dental devices, and more specifically, to intraoral dental irrigation appliances and methods of manufacturing the same.

BACKGROUND

Maintaining proper oral hygiene generally requires adhering to a comprehensive cleaning routine. Among other things, cleaning routines can help in preventing gingivitis, periodontal disease, cavities, or other diseases and tooth decay. In addition, this cleaning can aid in the healing of oral tissues that have been damaged due to one or more conditions, such as gingivitis, periodontal disease, oral injuries, and oral surgery. Typical cleaning methods may include at least one of brushing, flossing, interdental cleaning, irrigation, and other treatments/procedures.

As can be appreciated, various oral conditions may require specifically tailored cleaning techniques. For instance, an individual may be restricted from brushing one or more areas of the teeth after a surgery, treatment, or due to some other oral pathology. In this example, the individual may be directed to use special tools and/or appliances when cleaning the mouth or teeth. In some cases, recommended cleaning routines, especially when using these special tools and/or appliances, can be cumbersome, time consuming, involved, and even complicated. As a result, an individual may consider the cleaning routine as an inconvenience and cease the activity altogether.

In other cases, an individual may be diligent in adhering to a particular cleaning regimen, but may not be sufficiently cleaning all of the areas required for proper care. For example, an individual may not be capable of seeing that certain areas, especially toward the posterior (e.g., molars), are not being sufficiently cleaned. In this example, the individual may not know that areas are being missed. Additionally, these areas may be difficult to reach for the individual, and without training as a hygienist or other dental professional, the individual may simply elect to clean a different area of the mouth.

In addition, an individual who may not possess the skills necessary for cleaning the teeth in a particular manner can accidentally cause damage to the teeth and/or areas of the mouth. Examples of accidental damage may include chipping of the teeth, punctured gingiva, inflammation, lacerations, and the like. Current teeth cleaning products and solutions fail to address all of the issues provided above, especially in individuals having periodontal or other oral pathology.

SUMMARY

It is with respect to the above issues and other problems that the embodiments presented herein were contemplated.

In general, embodiments of the present disclosure provide a custom apparatus, or appliance, for irrigating areas of a mouth. In some embodiments, the appliance may serve a dual purpose of an occlusal guard (e.g., for bruxism, etc.) as well as an oral hygiene irrigation device. The appliance may be custom manufactured to treat specific treatment areas of the teeth and/or mouth. By way of example, a clinician manufacturing the appliance may position one or more irrigant exit ports at patient areas of need.

In any event, the appliance may be manufactured from one or more materials (e.g., ethyl methacrylate, methylmethacrylate, vinyl, polyvinyl, plastic, thermoplastic, combinations thereof, and the like) and may include a series of micro-channels and/or fluid chamber(s) that are configured to direct an irrigant via at least one path. These micro-channels may be configured to direct the irrigant to a number of irrigation sites adjacent to one or more teeth. Additionally or alternatively, the micro-channels and/or fluid chamber(s) may include an arrangement or geometry configured to increase at least one of a velocity and turbulence of a fluid passed therethrough. For example, at least a portion of the micro-channels and/or fluid chamber(s) may include one or more bends, angles, narrowing sections, expanding sections, reservoir areas, etc., and/or combinations thereof.

In some embodiments, the micro-channels and/or fluid chamber(s) may be operatively connected to an irrigant inlet port. The irrigant inlet port may be configured to receive an irrigant or other fluid supply that is to be applied to the treatment areas. For example, the inlet port may receive at least one fluid provided by a fluid supply or fluid source. Examples of a fluid source may include, but are not limited to, a water irrigation device, a Waterpik® brand water flosser, a pressurized water source (e.g., a tap, faucet, etc.), combinations thereof, and the like.

In some embodiments, a custom apparatus is provided that can serve the dual purpose of an occlusal guard for bruxism as well as an irrigating device for oral hygiene. The appliance may be ideal for irrigating areas of the mouth including, but not limited to, interproximal areas, furcations, root surfaces, orthodontics, and other areas. Use of this irrigation appliance may be especially beneficial following periodontal surgery. For example, when a fluid supply source is fluidly-connected to the appliance, fluid can be conveyed to multiple areas of a mouth substantially simultaneously. This irrigation can save time in cleaning individual areas via traditional cleaning techniques (e.g., those techniques that may address only one area at a time) such as using a water irrigation device having a single fluid outlet or port. Moreover, the appliance does not need to be constantly moved within the mouth. Once the appliance is inserted into position, the fluid may be conveyed to multiple areas of the mouth via a single inlet port and multiple custom-configured exit, or outlet, ports.

The appliance may be created by obtaining three-dimensional ("3D") information about patient's mouth or a portion thereof. For example, custom impressions may be taken and bite registrations made which can be used to form plaster and/or stone study models of the patient. In another example, a 3D scan may be made of the mouth and a 3D model may be created from the 3D scan. In any event, the study models may be used to design a custom, or individualized, irrigation system within the occlusal guard that is specific to the patient's dentition and areas most in need (e.g., furcation food traps, periodontal areas, etc.).

In one embodiment, an initial wax-up of the irrigation system may be made by using specifically gauged wire wax. Individual wax wires can be arranged (e.g., welded, attached, positioned, etc.) at desired locations along or adjacent to portions of the teeth and/or mouth, such as interproximal areas, and with specific angulation that can be determined by a clinician as the most therapeutic for the patient. These wires may protrude laterally from the buccal and lingual surfaces of the dentition and may eventually become the exit channels and/or ports for the irrigant. Next, a larger size wax wire or ribbon wax may be bent in a sinusoidal pattern and made to follow the general "U" shape pattern of the mouth while remaining in contact with the wire exit channels formed. This may be achieved by placing a single SP wire on the occlusal surface or dual SP wires on the buccal and lingual pictures. Once suitable location is achieved, the SP wire may be attached (e.g., welded, affixed, or otherwise connected) to the exit channels. This will form a wider central chamber that mirrors and/or follows the dentition with narrower periodic exit channels protruding off the central canal and attaching to the dentition. This pattern is based on fluid dynamic principals that work to increase the turbulence and velocity of the irrigant. Additionally or alternatively, it may be beneficial to extend the SP wire a distance (e.g., 1-2 mm, or more) bilaterally past a distal portion of the last exit shaft. In doing so, back flow can be created and a more even distribution of irrigant through all the channels may be achieved.

In some embodiments, a custom convex or concave port may be formed out of dental wax depending on what irrigation device the guard will be attached to. This port may be attached and/or welded to the central canal on the buccal surface near the patient's midline. Once the wax microchannel irrigation system is set, the model may be coated with a separating agent and placed in a containment mold. Once the separator has dried, a cold cure product that is approved and suitable for an occlusal guard such as, but not limited to, ethyl methacrylate, methylmethacrylate, vinyl, polyvinyl, plastic, combinations thereof, and the like, can be mixed and poured while in its liquid state into the mold containing the model. Upon curing, the wax irrigation system may be melted away using a standard boiling or heating process. The appliance may then be "broken out," prepped, finished, and polished (e.g., for use by a patient, etc.).

In some embodiments, the device may be created by taking custom impressions and bite registration which can be used to form plaster/stone study models of a patient. These study models may be used to design an individualized irrigation system within the occlusal guard that is specific to the patient's dentition and areas most in need (e.g., furcation food traps, etc). First the study models are placed on an articulator using the bite registration of the patient. Once set, an initial wax up of the micro irrigation system can be completed by using specifically gauged bendable micro tubing. Individual micro tubing may be bent in a sinusoidal pattern and welded at the desired locations on the buccal and lingual surfaces following the "U" shape pattern of the mouth. Also a custom convex or concave port can be formed out of dental wax depending on what irrigation device the guard will be attached to. From here wax can be placed over the tubing and model where it is "waxed up." Next the model is invested in a flask with plaster and packed with night guard material and processed. Once the guard has cured it can be broken out from the model. The clinician can at this point drill holes through the inner side of the guard at interproximal locations or wherever necessary, to create individual channels to the tubing. The guard can then be prepped, finished, and polished. In some embodiments, after the device is waxed up, it may be processed by vacuum form.

The phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising," "including," and "having" can be used interchangeably.

The term "means" as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1A:
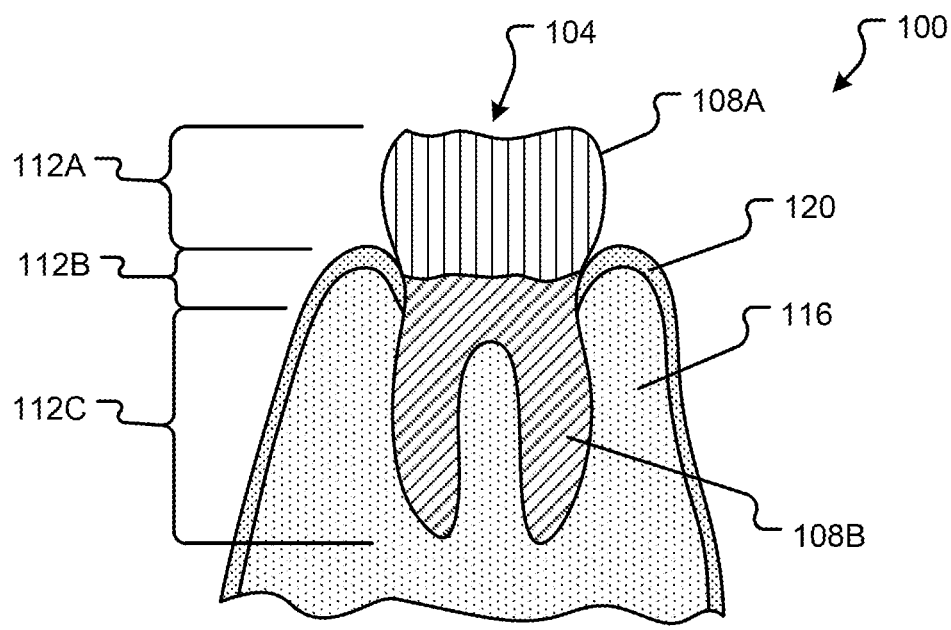
FIG. 1A is a cross-sectional view of a tooth and normal gingiva in accordance with embodiments of the present disclosure.

Referring to FIG. 1A, a cross-sectional view of a tooth 104 and normal gingiva 120 (100) is shown in accordance with embodiments of the present disclosure. The tooth 104 may include an enamel portion 108A and a cementum portion 108B. Additionally or alternatively, the tooth 104 may comprise a crown 112A, a root 112C, and a neck 112B disposed between the crown 112A and the root 112C. As shown in FIG. 1A, the tooth 104 is attached to the bone 116 of an animal (e.g., a human, etc.) via the root section 112C. In some embodiments, the tooth 104 may include at least one exposed portion and one or more unexposed portions. At least one groove, recess, or sulcus may exist at a point where the gingiva 120 meets a portion of the tooth 104. Typical oral hygiene routines may include flossing, brushing, and/or otherwise cleaning these areas of the teeth. In healthy teeth, the root 112C is substantially unexposed and the gingiva 120 may even cover an entirety of the root 112C.

Figure 1B:
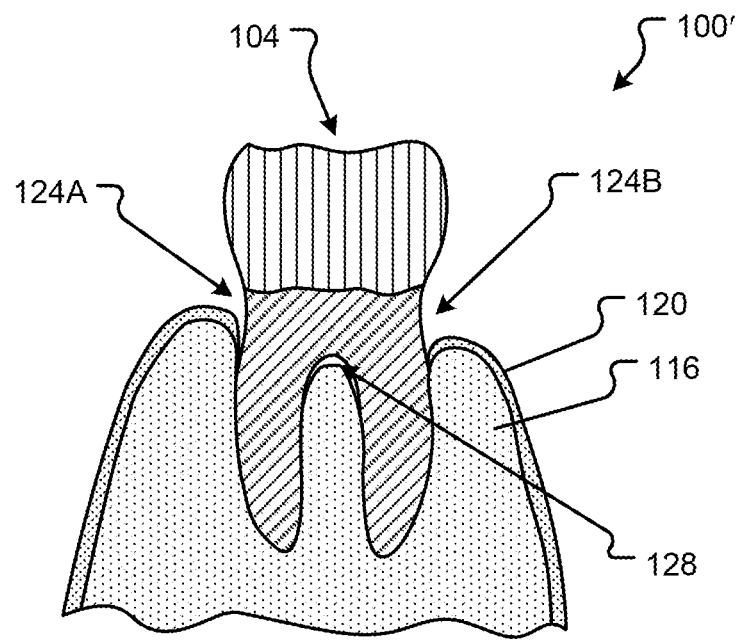
FIG. 1B is a cross-sectional view of a tooth and recessed gingiva in accordance with embodiments of the present disclosure.

FIG. 1B shows a cross-sectional view of a tooth 104 and recessed gingiva 120 (100') in accordance with embodiments of the present disclosure. In some embodiments, the gingiva 120 may be recessed due to surgery, disease, trauma, age, genetic condition, other issue, and/or combinations thereof. As shown in FIG. 1B, the recessed gingiva 120 may expose more areas of the tooth 104, such as the neck 112B and/or root 112C sections. In some cases, a furcation 128 of the tooth 104 may be at least partially exposed by the recession of the gingiva 120. In any event, one or more sulci 124A, 124B (e.g., a first sulcus 124A and a second sulcus 124B, etc.) may be revealed by the recession of the gingiva 120 and/or the decay of the bone 116. These areas typically require special attention during cleaning as plaque, bacteria, food, and/or other debris may accumulate in these portions of the teeth.

Figure 2A:
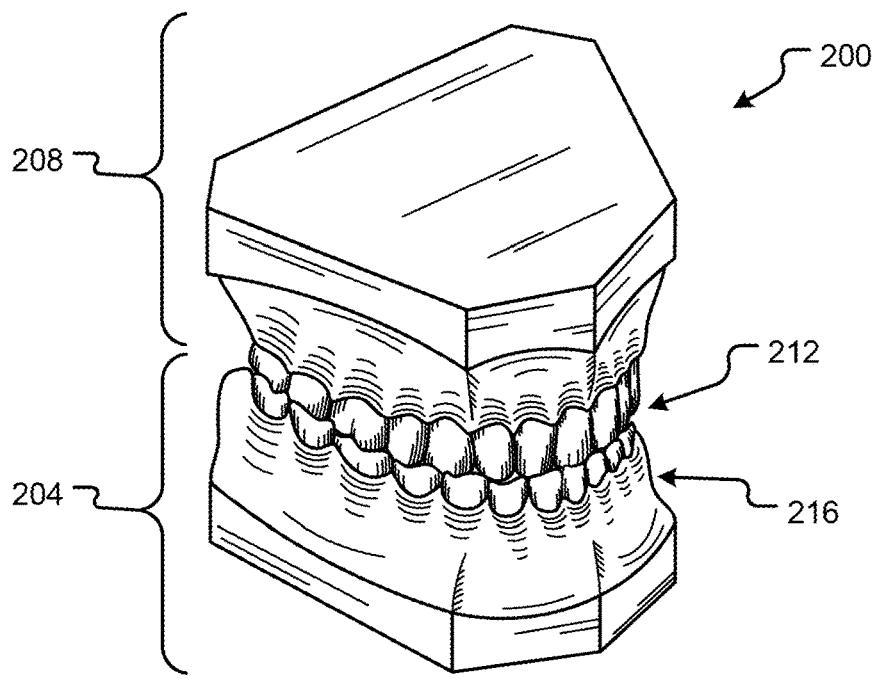
FIG. 2A is a perspective view of a study model in accordance with embodiments of the present disclosure.

FIG. 2A is a perspective view of a study model 200 in accordance with embodiments of the present disclosure. Creating the study model 200 may include taking an impression of a subject's teeth and making a physical model of an upper and/or lower portion of the teeth. In some embodiments, the subject's teeth may be scanned (e.g., via X-ray, or other scan, etc.) and a 3D model may be created of the subject's teeth. This 3D model may be created virtually, such as in a computer aided design ("CAD") program and/or physically, such as a model made via 3D printing techniques and/or other manufacturing methods. In any event, the study model 200 may include a complete or partial model of the teeth 212 and gums, or gingiva 216, which may require attention and/or care. For example, the study model 200 can allow for accurate and custom channels, ports, and/or fluid paths to be created for directing irrigation fluid to particular areas of the teeth and/or mouth of a subject.

Figure 2B:
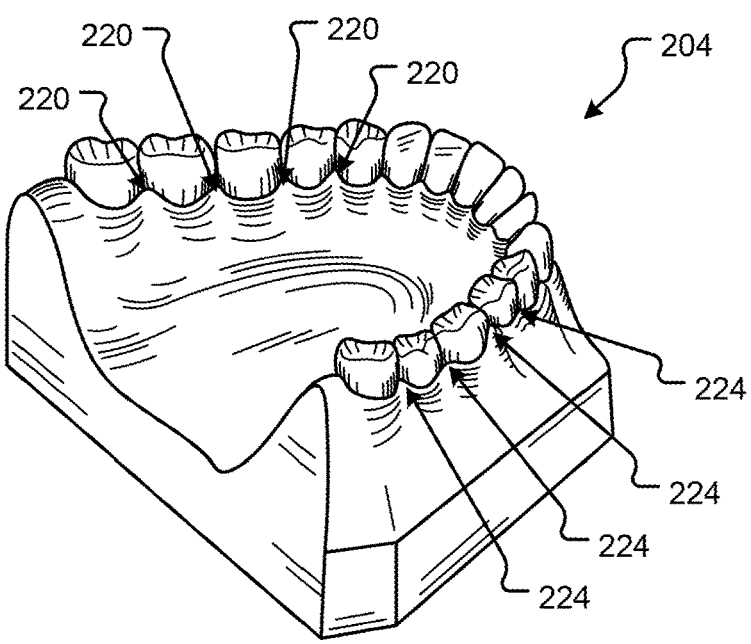
FIG. 2B is a perspective view of a study model lower portion in accordance with embodiments of the present disclosure.

FIG. 2B is a perspective view of a study model lower portion 204 in accordance with embodiments of the present disclosure. Although embodiments of the present disclosure will be described in conjunction with the study model lower portion 204, the present disclosure anticipates creating a dental appliance for the lower and/or upper portion of the teeth of a subject using one or more of a study model lower portion 204 or a study model upper portion 208. As shown, the study model lower portion 204 may provide a 3D representation of desired areas of irrigation, i.e., treatment areas. Typically, these treatment areas may include one or more sulci 220, 224. The study model can include lingual sulci 220 and facial or buccal sulci 224. It should be appreciated that the lingual sulci 220 and/or the buccal sulci 224 may exist at any area between one or more teeth 212 in the study model lower portion 204.

Figure 3A:
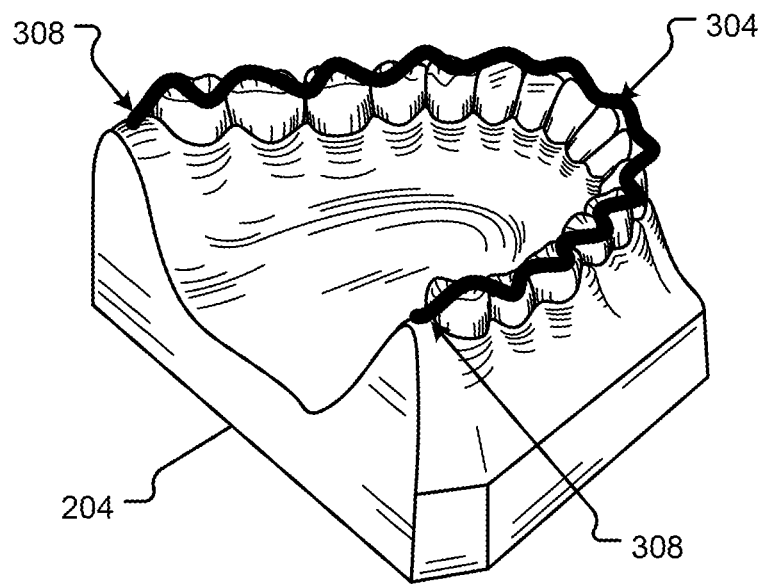
FIG. 3A is a perspective view of a fluid chamber substrate disposed along an occlusal path of a study model lower portion in accordance with embodiments of the present disclosure.

FIG. 3A is a perspective view of a fluid chamber substrate 304 disposed along an occlusal path of a study model lower portion 204 in accordance with embodiments of the present disclosure. The fluid chamber substrate 304 may be offset from the occlusal surface of the teeth some distance. This offset may be created by a length of fluid channel substrates 312 (shown in FIGS. 3B-3D) that have been arranged at the one or more treatment areas. In some embodiments, the fluid chamber substrate 304 may be a wax, or equivalent, material that is arranged along a "U-shaped" path following the curvature of the teeth 212. The fluid chamber substrate 304 may be configured with one or more bends along this path. In some embodiments, these one or more bends may be formed in a sinusoidal and/or an undulated fashion. In one embodiment, the undulations in the fluid chamber substrate 304 may provide a tortuous path for a fluid to follow, creating turbulence in the irrigation system and intraoral dental irrigation appliance. In some embodiments, the fluid chamber substrate may be arranged to extend beyond one or more of the treatment area irrigation outlets. This extension portion 308 may provide for a substantially equal distribution of irrigant and/or pressure through various outlet ports of the irrigation appliance.

Figure 3B:
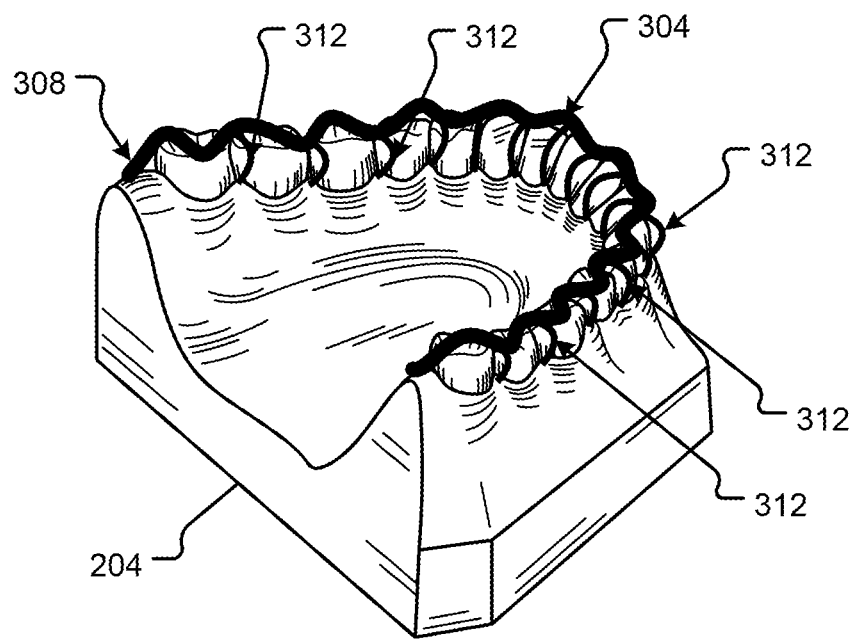
FIG. 3B is a perspective view of a fluid channel substrates connected to a fluid chamber substrate disposed along an occlusal path of a study model lower portion in accordance with embodiments of the present disclosure.

FIG. 3B is a perspective view of a plurality of fluid channel substrates 312 connected to a fluid chamber substrate 304 disposed along an occlusal path of a study model lower portion 204 in accordance with embodiments of the present disclosure. In some embodiments, the fluid channel substrates 312 may be created prior to disposing the fluid chamber substrate 304 thereon. In this example, the fluid channel substrates 312 may support the fluid chamber substrate 304 above, or offset from, the occlusal surface of the teeth 212. Similar to the fluid chamber substrate 304, the fluid channel substrates 312 may be a wax, or equivalent, material. The fluid channel substrates 312 may be welded, affixed, or otherwise attached to the fluid chamber substrate 304. In one example, the fluid channel substrates 312 may be melted to the fluid chamber substrate 304 to form a fluidly connected path.

In some embodiments, the fluid channel substrates 312 may be manufactured from a smaller gauge or diameter of material than the fluid chamber substrate 304. The sizing of the channels and/or substrates 312 may be configured to direct and/or channel fluid through the finished irrigation appliance.

Figure 3C:
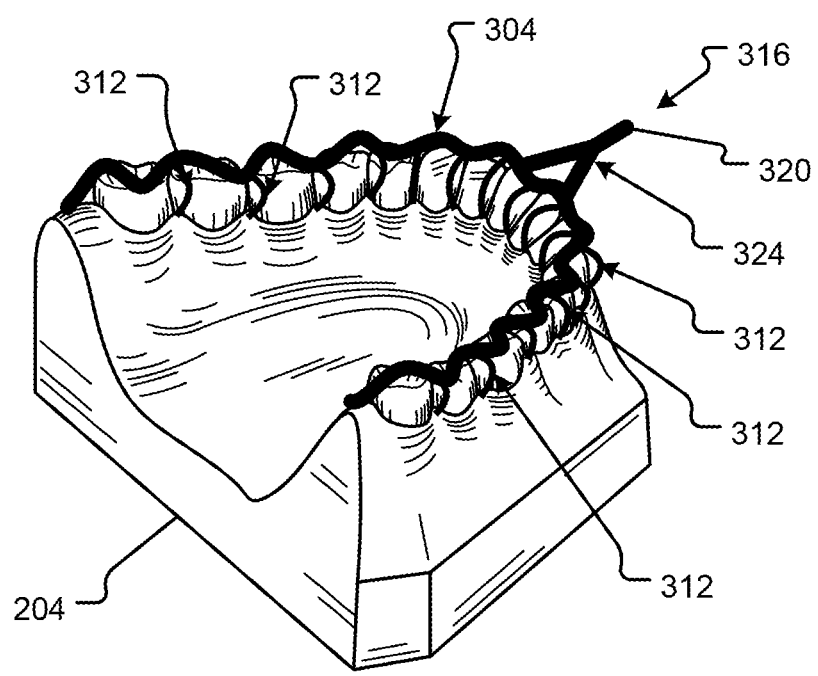
FIG. 3C is a perspective view of an irrigation system model having a fluid port arranged about a study model lower portion in accordance with embodiments of the present disclosure.

FIG. 3C is a perspective view of an irrigation system model having a fluid port 316 arranged about a study model lower portion 204 in accordance with embodiments of the present disclosure. The fluid port 316 may be made from a similar material and/or size to that of the fluid chamber substrate. In some embodiments, the fluid port 316 may be made from a wax material having a larger gauge than the fluid chamber substrate 304. Although shown attached to the fluid chamber substrate 304 at a labial, or front, area of the study model lower portion 204, the fluid port 316 may be attached at any location(s) along the fluid chamber substrate 304. The fluid port 316 may be attached to the fluid chamber substrate 304 at one or more points. In one embodiment, the fluid port may be bifurcated and attached at two different locations of the fluid chamber substrate 304. For instance, an inlet 320 of the fluid port 316 may be connected to the fluid chamber substrate 304 via a fluid port bifurcation 324.

The fluid port 316 may be shaped or otherwise configured to receive a fluid from a fluid supply or source. In one embodiment, the fluid port 316 may have an inlet 320 that is configured to mate with a fluid supply (e.g., a Waterpik® brand water flosser, a hose connected to a faucet, etc.). The inlet 320 may be shaped as a nozzle, a cone, a taper, a straight coupling, portions and/or combinations thereof, etc. For example, when shaped with a taper, the taper of the inlet 320 may proceed from a larger diameter at an outer location (e.g., furthest from the teeth) to a smaller diameter at an inner location (e.g., adjacent to the teeth), or vice versa. In one embodiment, the shape of the inlet 320 may be configured to match or selectively interconnect with a fluid supply.

Figure 3D:
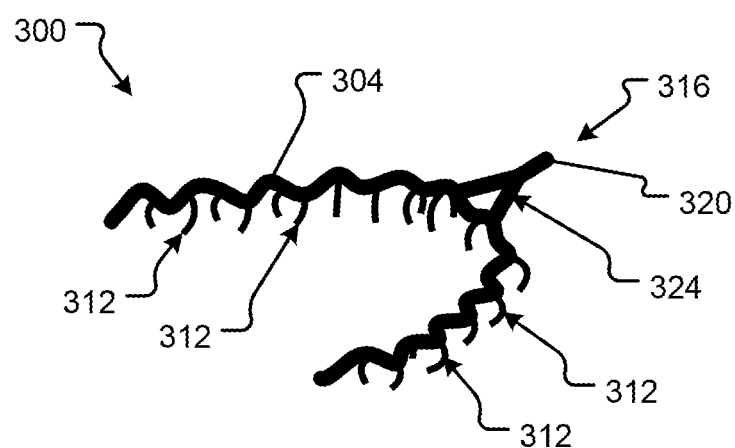
FIG. 3D is a perspective view of an irrigation system model having a fluid port separated from a study model in accordance with embodiments of the present disclosure.

FIG. 3D is a perspective view of an irrigation system model 300 having a fluid port 316 in accordance with embodiments of the present disclosure. The irrigation system model 300 is shown separate from a study model 200 for clarity. As shown, the irrigation system model 300 may include one or more fluid channel substrate branches 312, a fluid chamber substrate 304, and at least one fluid port 316.

Figure 4A:
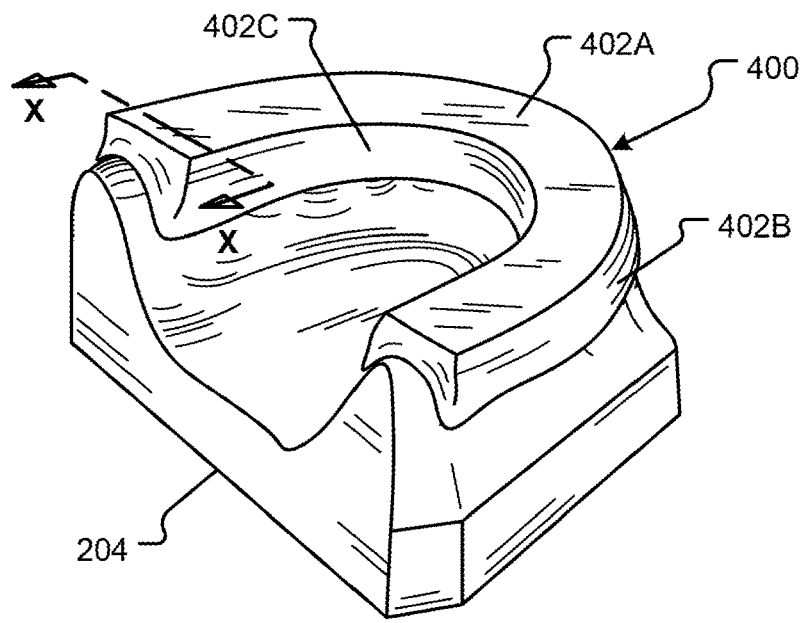
FIG. 4A is a perspective view of an intraoral dental irrigation appliance interconnected with a portion of a study model in accordance with embodiments of the present disclosure.

FIG. 4A is a perspective view of an intraoral dental irrigation appliance 400 removably attached to a study model lower portion 204 in accordance with embodiments of the present disclosure. The intraoral dental irrigation appliance 400 may include a body having an occlusal or biting wall 402A, a buccal or outer wall 402B, and a lingual or inner wall 402C. The walls 402A, 402B, 402C may comprise at least one appliance material having one or more thicknesses. In some embodiments, the intraoral dental irrigation appliance 400 may be molded, formed, or otherwise disposed around an irrigation system model 300. For example, a mold material may be added to the study model lower portion 204 and caused to fill in between areas of the model 204 and the irrigation system model 300. In the case of a wax irrigation system model 300, once the mold material cures, the wax irrigation system model 300 may be melted and a complete irrigation fluid path or system may be formed therein.

Figure 4B:
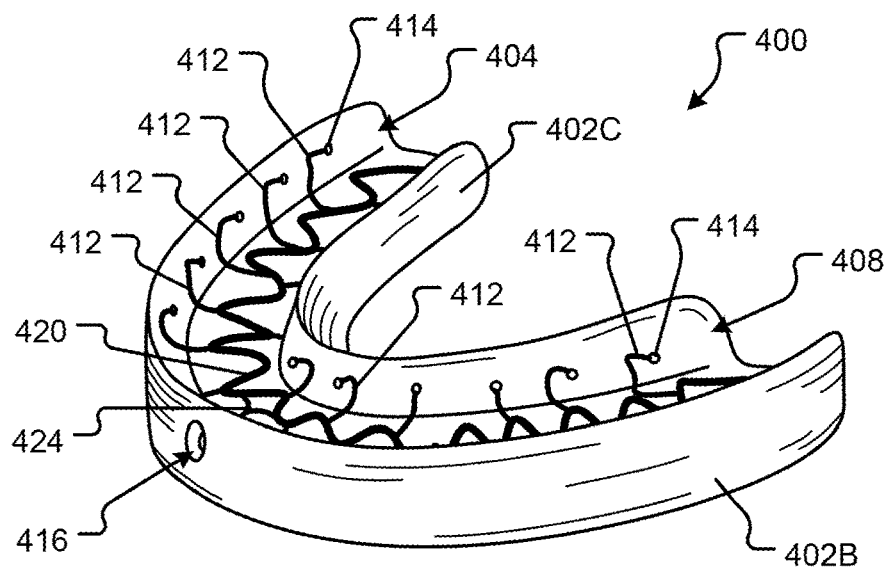
FIG. 4B is a perspective view of an intraoral dental irrigation appliance in accordance with embodiments of the present disclosure.

FIG. 4B is a perspective view of an intraoral dental irrigation appliance 400 in accordance with embodiments of the present disclosure. The intraoral dental irrigation appliance 400 is shown with a partially visible irrigation fluid path or system. This system may correspond to a void, chambers, channels, and/or other volume left by the wax irrigation system model 300 after it has been removed (e.g., via melting, etc.). The irrigation fluid path or system comprises the at least one fluid chamber 420, fluid channels 412, and fluid channel outlets 414. The irrigation fluid system may be at least partially contained in the body of the intraoral dental irrigation appliance 400. For example, the fluid chamber 420 may be contained within the occlusal wall 402A of the appliance 400. The fluid channels 412 may be contained in a portion of the occlusal wall 402A and continue to be contained in at least one of the buccal or lingual walls 402B, 402C. In any event, the fluid channels 412 are fluidly connected to the fluid chamber 420 and are configured to direct fluid from the chamber 420 to at least one fluid channel outlet 414.

As shown in FIG. 4B, a series of fluid channel outlets 414 are disposed on an interior buccal surface 404 of the buccal wall 402B and along an interior lingual surface 408 of the lingual wall 402C of the appliance 400. The fluid channel outlets 414 may correspond to one or more treatment areas of a subject dentition. As provided herein the fluid channel outlets 414 may be configured as one or more fluid directing shapes. These fluid directing shapes may include one or more geometries, variations in geometry, and/or other features. In some embodiments, the fluid chamber 420 may correspond to one or more voids left in the appliance 400 by a removal of the fluid chamber substrate 304 of the irrigation system model 300. In one embodiment, fluid channels 412 may correspond to one or more voids left in the appliance 400 by a removal of the fluid channel substrates 312 of the irrigation system model 300. Additionally or alternatively, the fluid channel outlets 414 may correspond to one or more holes, attachment points, voids, or areas left in the appliance 400 by a removal of the fluid channel substrates 312 of the irrigation system model 300.

In some embodiments, the intraoral dental irrigation appliance 400 may include at least one fluid port 416. As shown in FIG. 4B, the fluid port 416 is disposed on a portion of the buccal wall 402B of the appliance 400. The fluid port 416 may correspond to one or more holes, attachment points, voids, or areas left in the appliance 400 by a removal of the model fluid port 316 of the irrigation system model 300 (e.g., via melting, etc.). The fluid port 416 may be fluidly connected to the fluid chamber 420 via one or more inlet connections 424. FIG. 4B shows a portion of a bifurcated inlet connection 424 fluidly connecting the fluid port 416 to the fluid chamber 420. As provided above, the fluid port 416 may be shaped or otherwise configured to receive a fluid from a fluid supply or source. In one embodiment, the fluid port 416 may have an inlet that is configured to mate with a fluid supply (e.g., a Waterpik® brand water flosser, a hose connected to a faucet, etc.). The inlet of the fluid port 416 may be shaped as a nozzle, a cone, a taper, a straight coupling, portions and/or combinations thereof, etc. For example, when shaped with a taper, the taper of the fluid port 416 may proceed from a larger diameter at an outer location (e.g., furthest from the teeth) to a smaller diameter at an inner location (e.g., adjacent to the teeth), or vice versa. In one embodiment, the shape of the fluid port 416 may be configured to match or selectively interconnect with a fluid supply.

Figure 5:
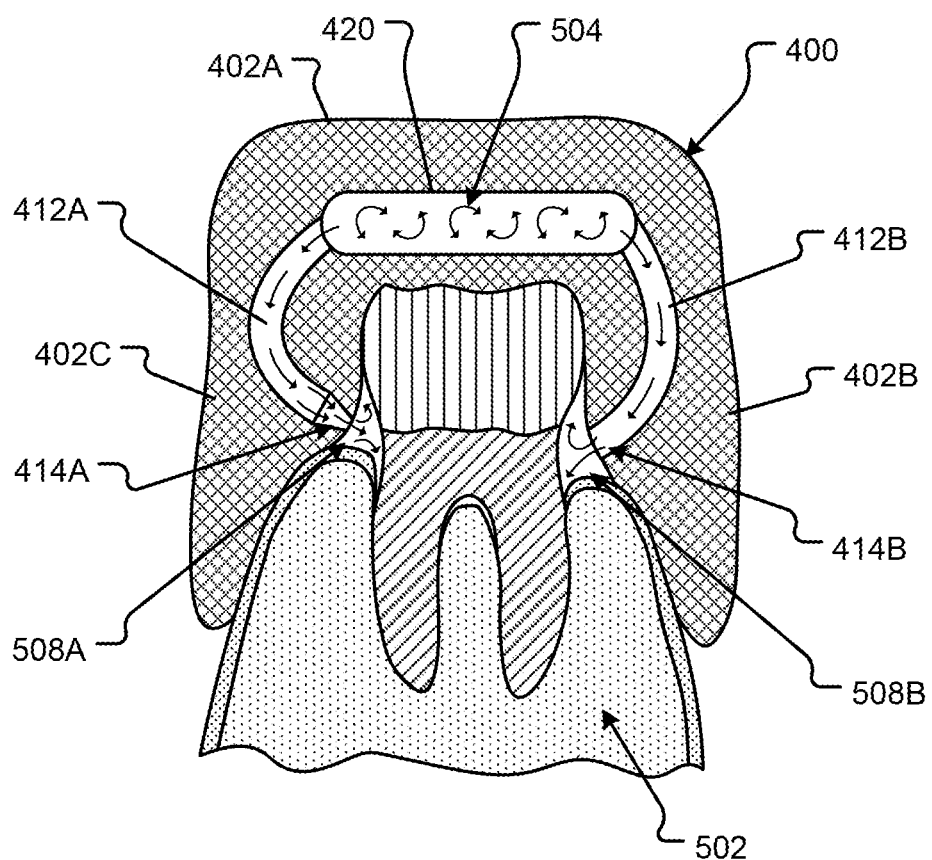
FIG. 5 is a cross-sectional view of an intraoral dental irrigation appliance at least partially surrounding a tooth viewed from arrow "X-X" in FIG. 4A in accordance with embodiments of the present disclosure.

FIG. 5 is a cross-sectional view of an intraoral dental irrigation appliance 400 at least partially surrounding a portion of a subject dentition 502 (e.g., tooth, gingiva, bone, etc., or a representative study model portion 204, etc.) in accordance with embodiments of the present disclosure. As shown, FIG. 5 may correspond to a cross-section taken from arrow "X-X" in FIG. 4A. In any event, once the irrigation system model 300 is created and the irrigation appliance 400 is created, the irrigation system model 300 defines a path for directing fluid to one or more areas of the mouth. In one embodiment, the irrigation system model 300 may be made from a wax material and melted from a cured irrigation appliance member 400. In this case, the melted irrigation system model 300 can leave a void in the irrigation appliance 400. The void may define the fluid chamber 420 and one or more fluid channels 412A, 412B. In some embodiments, the fluid chamber 420 may be configured to receive a fluid under pressure. The geometry of the fluid chamber 420 may cause the pressurized fluid flowing therein to experience a turbulence, or turbulent flow 504. The fluid channels 412A, 412B may direct the fluid from the fluid chamber 420 to a number of cleansing cavities 508A, 508B formed between a portion of the irrigation appliance 400 and the tooth. As the fluid is provided to the irrigation device 400, the fluid may be directed to the cleansing cavities 508A, 508B and/or treatment sites via one or more fluid channels 412A, 412B. In one embodiment, the treatment sites may include occlusal and/or other areas/surfaces of the teeth. It is an aspect of the present disclosure that the fluid may then flush along the gingiva and out of a portion of the irrigation appliance 400 (e.g., the back of the appliance, via a gutter, or other fluid urn, etc.). In operation, the fluid may then exit the mouth of a patient using the device 400.

Each fluid channel 412A, 412B may include a portion, or end, connecting the fluid channel to the fluid chamber and an outlet 414A, 414B disposed adjacent to the treatment site. The outlet 414A, 414B may be configured with a nozzle outlet 414A as shown in the first fluid channel outlet 412A and/or as a substantially straight exit port 414B shape as shown in the second fluid channel 412B. In some embodiments, the nozzle of 414A may be configured to increase an exit velocity of the fluid from the fluid channel 412A. For example, the first fluid channel 412A includes a nozzle-shaped first fluid channel outlet 414A configured to focus, and/or increase a pressure of, fluid toward the cleansing cavity. As another example, the second fluid channel 412B includes a substantially straight second fluid channel outlet 414B. As shown in FIG. 5, the fluid may move in one or more paths illustrated by the arrows in each chamber and channel. Among other things, this fluid flow can clean the area of debris, plaque, bacteria, and/or other material. In one embodiment, the geometry of the irrigation system, i.e., the voids left behind from a melted irrigation system model 300, may provide for turbulent flow in the fluid chamber and a substantially laminar and/or directed flow in each fluid channel 412A, 412B. It is an aspect of the present disclosure that, in use, the fluid may flush the debris and/or other material along a portion of the appliance 400 and out of a subject's mouth.

Figure 6:
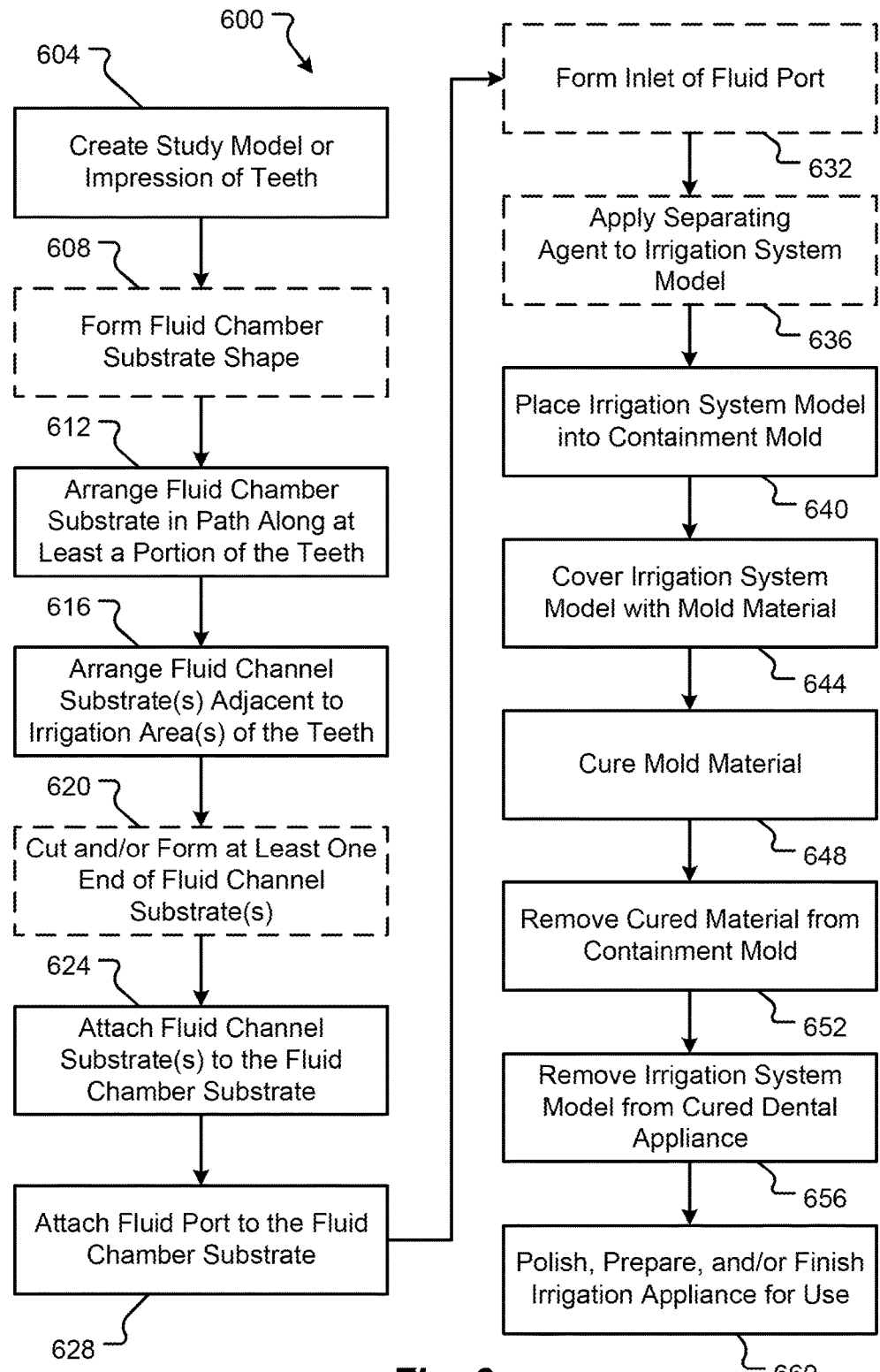
FIG. 6 is a flow or process diagram depicting a first method for manufacturing an intraoral dental irrigation appliance in accordance with embodiments of the present disclosure.

FIG. 6 is a flow or process diagram depicting a first method 600 for manufacturing an intraoral dental irrigation appliance 400 in accordance with embodiments of the present disclosure. The method 600 may begin by creating a study model and/or taking an impression of the teeth (step 604). Creating the study model can include, but is not limited to, preparing a 3D CAD model (e.g., from a scan of the teeth, a measurement of the teeth, etc.), making a plaster cast of the teeth, or otherwise preparing a physical model of a patient's teeth.

Once a study model 200 is created of a patient's teeth, a clinician may determine treatment sites for arranging the fluid channel substrates 312. These treatment sites or areas may be determined based on exam results, desired areas of treatment, doctor recommendations, and/or industry standards. In some embodiments, the treatment areas may be determined automatically via a computer and analysis system (e.g., via X-ray, laser detection machine, light machine, diagnostics tool, combinations thereof, and the like).

As an optional step, the fluid chamber substrate 304 may be formed with one or more bends and/or undulations (step 608). In one embodiment, the bends and/or undulations may serve to create turbulent fluid flow within a created fluid chamber 420 in the appliance 400.

The next two steps disclose arranging the fluid chamber substrate 304 and the fluid channel substrates 312 along a portion of the teeth (steps 612, 616). It should be appreciated, that depending on the embodiment, any of the method 600 steps may be exchanged, made optional, followed in a different order than shown, removed, and/or repeated. The fluid chamber substrate 304 may be arranged to follow the general "U-shaped" curvature of the dentition of the patient (e.g., that may be represented by the study model 200, etc.).

In one embodiment, the fluid channel substrates 312 may be disposed at or adjacent to each treatment area. In some embodiments, the fluid channel substrates 312 may be fused, glued, or otherwise attached to the necessary study model 200 locations. Additionally or alternatively, the fluid channel substrates 312 may be used to support the fluid chamber substrate 304 apart from (e.g., via a distance, etc.) the occlusal surface of the teeth. The fluid channel substrates 312 may be cut from a reel or length of material (step 620). Additionally or alternatively, the fluid channel substrates 312 may be cut and/or sized to match particular areas of the dentition. In one embodiment, at least one end of the fluid channel substrates 312 may be formed into one or more shapes. For instance, a cutting tool may incorporate a conical, or tapered, cutting portion that is configured to form a nozzle shape (e.g., nozzle outlet 414A, shape, etc.) at least at one end of the fluid channel substrate 312.

In any event, the fluid channel substrates 312 may be connected to the fluid chamber substrate 304 at various locations along the fluid chamber substrate 304 (step 624). This connection may include ensuring that an area adjacent to an end of the fluid channel substrate 304 (e.g., the end opposite the exit port end of the fluid channel) is directly in contact with the fluid chamber substrate 304. In one example, this attachment may be facilitated via an adhesive, fusion, mechanical connection, etc.

The method 600 may continue by attaching a fluid port 316 to the fluid chamber substrate 304 (step 628). Among other things, the fluid port 316 may be configured to receive an irrigant or other fluid at a location that is accessible via a user. In one embodiment, the fluid port 316 may extend from the fluid chamber substrate 304 and in a direction away from the dentition. Once the irrigation appliance 400 is created, the fluid port 416 may provide the interface to an irrigation source or fluid supply. This interface may include forming an inlet that is configured to receive and/or mate with a water flosser, hose, nozzle, or other outlet of the fluid supply (step 632).

In some embodiments, the method 600 may continue by applying a separating agent or material to the irrigation system model 300 and/or at least a portion of the study model 200 (step 636).

Next, the method 600 continues by molding the irrigation appliance 400 around the irrigation system model 300 and at least a portion of the study model 200. In one embodiment, the irrigation system model and/or at least a portion of the study model 200 may be inserted into a containment mold (step 640). The containment mold may be in the form of a container that is configured to at least partially surround the irrigation system model and the at least a portion of the study model 200. The method 600 may continue by covering the irrigation system model 300 and at least a portion of the study model 200 with a mold material (step 644). The method 600 continues by curing the mold material (step 648). Typical mold materials may be cured via, time, temperature, reaction, combinations thereof, and the like. Once the mold is cured, the material may be removed from the mold containment (step 652). At this point, the irrigation system 300, that is, the fluid channel substrates 312 and fluid port material 316 attached to the fluid chamber substrate 304 can be removed from the cured irrigation appliance 400 (step 656). In one embodiment, the irrigation system 300 may be a wax material and removing the irrigation system 300 from the cured irrigation appliance 400 may include subjecting the irrigation system 300 to temperature (e.g., via a boiling process, etc.). Once the irrigation system 300 is removed, or melted, from the cured irrigation appliance 400, a number of voids may remain in the irrigation appliance forming a fluid network having a fluidly-connected fluid chamber 420, a number of fluid channels 412, fluid outlets 414, and at least one fluid port 416. The irrigation appliance 400 may then be prepared for use, for example, by a patient or user (step 660). Preparation may include at least one of sizing, machining, cutting, and/or polishing one or more areas of the appliance 400. Additionally or alternatively, preparation may include at least one of cleaning the appliance 400, fitting the appliance 400, and testing the appliance 400. In one example, the irrigation appliance 400 may serve multiple purposes. For instance, the irrigation appliance 400 may serve as an occlusal guard for bruxism as well as a treatment/hygiene aid for directing fluid to treatment areas of the dentition.

Figure 7:
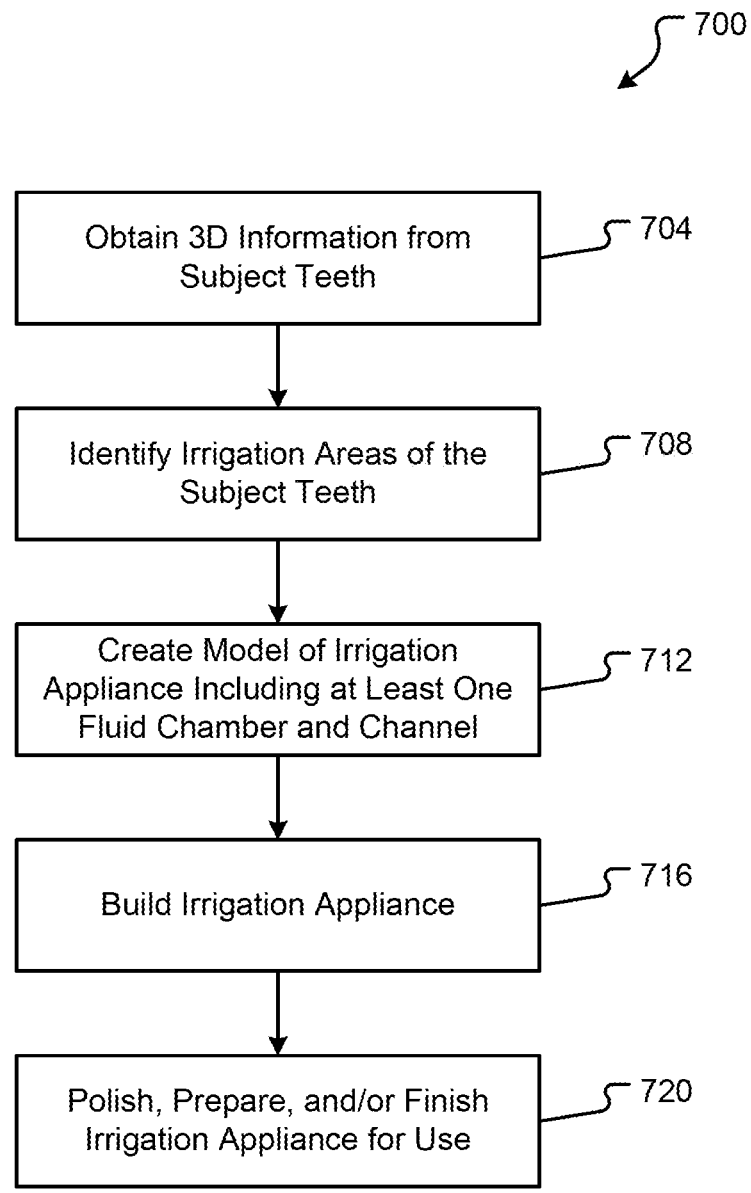
FIG. 7 is a flow or process diagram depicting a second method for manufacturing an intraoral dental irrigation appliance in accordance with embodiments of the present disclosure.

FIG. 7 is a flow or process diagram depicting a second method 700 for manufacturing an intraoral dental irrigation appliance 400 in accordance with embodiments of the present disclosure. The method 700 may begin by scanning a subject's teeth and creating a 3D model of the teeth. The 3D model may be created by CAD software (step 704). Next, the method 700 continues by determining the irrigation, or treatment, areas of the subject's teeth (step 708). The method 700 may then continue by creating a model of the irrigation appliance 400 having at least one fluid chamber (step 712). The irrigation appliance 400 may include a number of fluid channels 412 disposed adjacent to each determined treatment area. Next, the method 700 proceeds by building the irrigation appliance 400 (step 716). The irrigation appliance 400 may be built using a number of manufacturing techniques and/or processes. For example, the irrigation appliance 400 may be constructed via a 3D printing, fused deposition modeling (FDM), selective laser sintering (SLS), casting, molding, machining, and/or other prototyping and/or manufacturing process. After the irrigation appliance 400 has been built, the appliance 400 may be optionally polished, prepared, and/or finished for use (e.g., similar, if not identical, to the preparation described in conjunction with FIG. 6)(step 720).

In some embodiments, the fluid chamber substrate 304 may be arranged at a portion of the teeth attached to the fluid channel substrates 312 and treatment sites of a study model 200. The fluid chamber substrate 304 may have an undulated, or sinusoidal, shape. In some embodiments, the fluid chamber substrate 304 may be preformed or shaped to have bends, undulations, and/or other fluid directing features. Although typically disposed spaced apart from an occlusal surface of the teeth, the fluid chamber substrate 304 may be disposed along a facial, or buccal, portion of the teeth.

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference label.

Also, while the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others. For instance, various molding materials and/or process may be used. In one embodiment, thermal beads may be used to form the intraoral dental irrigation appliance 400 as disclosed herein.

The present disclosure, in various aspects, embodiments, and/or configurations, includes components, methods, processes, systems and/or apparatus substantially as depicted and described herein, including various aspects, embodiments, configurations embodiments, subcombinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and/or reducing cost of implementation.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Summary, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A dental irrigation appliance, comprising:
   a first member arranged to conform to a portion of a subject dentition;
   a chamber disposed within the first member and configured to receive and convey a fluid from a supply, wherein the chamber follows a curved path defined by the subject dentition, and wherein the chamber includes a plurality of bends formed in a sinusoidal pattern along the curved path;
   a plurality of channels disposed within the first member, each channel having a first end fluidly-connected to the chamber and an outlet end, wherein the plurality of channels are configured to direct fluid from the first end to the outlet end; and
   a port fluidly-connected to the chamber and configured to receive the fluid.

2. The dental irrigation appliance of claim 1, wherein the port includes an inlet disposed at an outer surface of the first member, the inlet having an opening diameter tapering to a smaller inner diameter adjacent to the chamber.

3. The dental irrigation appliance of claim 1, wherein the curved path is substantially U-shaped.

4. The dental irrigation appliance of claim 1, wherein the outlet end of each channel in the plurality of channels includes a nozzle shape configured to focus fluid expelled from the plurality of channels.

5. The dental irrigation appliance of claim 1, wherein the port includes an inlet having a feature configured to selectively interconnect with a fluid supply tool.

6. The dental irrigation appliance of claim 5, wherein the fluid supply tool is a tip of a water flosser.

7. The dental irrigation appliance of claim 1, wherein the first member is at least one of ethyl methacrylate, methylmethacrylate, vinyl, polyvinyl, thermoplastic, and plastic.

8. A dental irrigation appliance kit, comprising:
   at least one solid fluid channel substrate having a first gauge and length;
   a solid fluid chamber substrate having a second gauge and length, wherein the solid fluid chamber substrate is a portion of wax material, and wherein the solid fluid chamber substrate includes a plurality of bends preformed in a sinusoidal pattern along an entirety of the length of the solid fluid chamber substrate; and
   a solid port material.

9. The dental irrigation appliance kit of claim 8, wherein the at least one solid fluid channel substrate is a reel of wax material.

10. The dental irrigation appliance kit of claim 8, wherein the first gauge and length is less than the second gauge and length.

11. A dental irrigation appliance prepared by a process, comprising:
    providing an irrigation system, comprising:
      arranging a plurality of channel members at treatment sites of a dentition model;
      attaching a chamber member to each of the plurality of channel members, wherein the chamber member follows a curved path defined by the dentition model, and wherein the chamber member includes a plurality of bends formed in a sinusoidal pattern along the curved path; and
      attaching a port member to the chamber member;
    providing a mold material covering at least a portion of the irrigation system;
    curing the mold material; and
    removing the irrigation system from the mold material via melting the irrigation system from the mold material leaving a void in the mold material having a shape of the irrigation system.

12. The dental irrigation appliance of claim 11, wherein the arranging the plurality of channel members includes affixing an end of each channel member to the dentition model.

13. The dental irrigation appliance of claim 11, wherein the mold material is made from a monomer.

14. The dental irrigation appliance of claim 11, wherein the mold material is at least one of ethyl methacrylate, methylmethacrylate, vinyl, polyvinyl, thermoplastic, and plastic.

15. The dental irrigation appliance of claim 11, wherein curing the mold material includes subjecting the mold material to heat.

16. The dental irrigation appliance of claim 11, wherein the mold material is a cold cure material.

17. The dental irrigation appliance of claim 11, wherein removing the irrigation system includes boiling the dental irrigation appliance at a melting temperature of the irrigation system.

* * * * *